United States Patent [19]

Gruszecki et al.

[11] 4,092,335

[45] May 30, 1978

[54] DESALANYLTETAINE DERIVATIVES AND THE METHOD FOR THEIR PREPARATION

[75] Inventors: Wojciech Gruszecki; Edward Bordwski; Jerzy Gumieniak; Malgorzata Gumieniak, all of Gdansk; Maciej Smulkowski, Gdynia; Hanna Wojciechowska, Gdansk; Miroslaw Bobrowski, Bialystok, all of Poland

[73] Assignee: Politechnika Gdanska, Gdansk-Wrzcszcz, Poland

[21] Appl. No.: 739,347

[22] Filed: Nov. 5, 1976

Related U.S. Application Data

[63] Continuation of Ser. No. 491,651, Jul. 25, 1974, abandoned.

[30] Foreign Application Priority Data

Jul. 26, 1973   Poland .................................. 164319

[51] Int. Cl.$^2$ ...................... C07D 301/00; A01N 9/00
[52] U.S. Cl. .......................... 260/348.44; 260/332.2 A; 260/332.3 H; 260/346.73; 260/348.55; 260/348.58; 424/275; 424/278; 424/285
[58] Field of Search ....................... 260/348 C, 348.44

[56] References Cited

U.S. PATENT DOCUMENTS 3,794,564   2/1974   Lively et al. .......................... 260/348

*Primary Examiner*—A. Siegel
*Attorney, Agent, or Firm*—Haseltine, Lake & Waters

[57] ABSTRACT

The subject of this invention are the desalanyltetaine derivatives of the formula 1, wherein $R^1$ is a hydroxyl group or an arrangement of the formula 2, wherein $R^3$ is a hydrogen atom or an alkyl, aryl, aralkyl group and X is an acyl or alkyl group, $R^2$ is a hydrogen atom or an acyl group, and Z is an oxygen atom, hydroxylamine or hydrazine radical or their alkyl, aryl or aralkyl derivatives.

The method of the preparation of the derivatives according to the invention consists in treating the desalanyltetaine derivatives of the formula 1, where $R^1$ and $R^2$ have the above mentioned significance, and Z is an oxygen atom with hydroxylamine, hydrazine or their derivatives. A modification of the method consists in treating the desalanyltetaine of the formula 1, where $R^2$ and Z have the above mentioned significance, and $R^1$ is a hydroxyl group with the chloroethers.

Another modification of the method consists in the fact that the desalanyltetaine derivatives of the formula 1 where $R^1$ and Z have the above mentioned significance and $R^2$ is a hydrogen atom, are acylized by the proper carboxylic acids derivatives.

The advantage of the derivatives according to the invention is a wide spectrum of their activity as well as their low toxicity.

1 Claim, 1 Drawing Figure

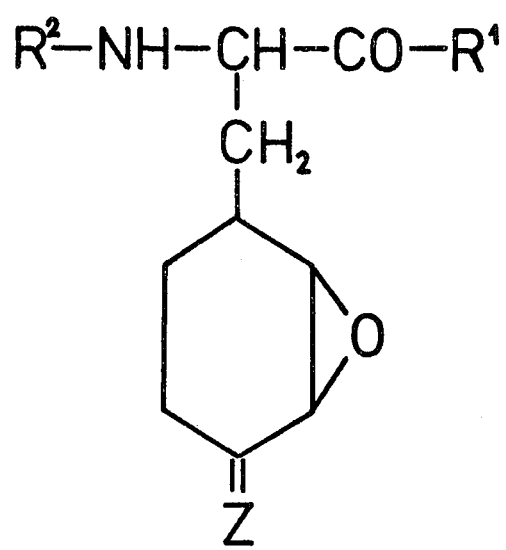
FORMULA 1
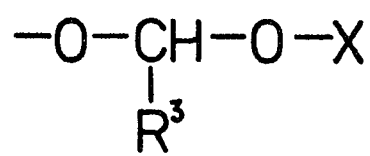
FORMULA 2

DESALANYLTETAINE DERIVATIVES AND THE METHOD FOR THEIR PREPARATION

This is a continuation of application Ser. No. 491,651 filed July 25, 1974, now abandoned.

The subject of this invention are the desalanyltetaine derivatives of the formula 1 wherein $R^1$ is a hydroxyl group or an arrangment of the formula 2 wherein $R^3$ is a hydrogen atom or an alkyl, aryl aralkyl group and X is an acyl or alkyl group, $R^2$ is a hydrogen atom or an acyl group, preferable an α-aminoacyl, acetylaminoacyl, substituted acetylaminoacyl group e.g. phenylacetylaminoacyl, phenoxyacetylaminoacyl, furylacetylaminoacyl and thienylacetylaminoacyl group or an acetyl or an analogically substituted acetyl group, and Z represents an oxygen atom, hydroxylamine or hydrazine radical or their alkyl derivatives e.g. methyl, ethyl or propyl or their aryl derivatives e.g. phenyl or aralkyl derivatives e.g. benzyl.

A group of antibiotics which are N-aminoacyl derivatives of desalanyltetaine has been known until now. These antibiotics have a wide spectrum of activity and a low toxity toward animals, including man. This toxity is due to the biochemical mechanism of their activity which solely inhibits the synthesis of the bacteria's cell-wall mureine.

The disadvantage of these antibiotics is their low stability and a rapid decomposition in the organism what causes that e.g. the tetaine is inactive in vivo. It is known at the same time that all possible changes in the reactive arrangement of the epoxidketone in the tetaine lead to the inactivation of the antibiotic.

The purpose of the invention is the obtaining of such desalanyltetaine derivatives which while conserving their antibiotic properties would have an increased stability giving the possibility of administering them as drugs. Within this purpose there is also the method of preparation of these derivatives.

According to the invention the desalanyltetaine derivatives of the formula 1 are characterized by the fact that $R^1$ represents a hydroxyl group or an arrangement of the formula 2, wherein $R^3$ represents a hydrogen atom, alkyl, aryl or aralkyl group, and X is an acyl or alkyl group, $R^2$ represents a hydrogen atom, acyl group preferable an α-aminoacyl, acetylaminoacyl, substituted acetylaminoacyl group e.g. phenylacetylaminoacyl, phenoxyacetylaminoacyl, furylacetylaminoacyl and thienylacetylaminoacyl group or an acetyl or an analogically substituted acetyl group, and Z represents an oxygen atom, hydroxylamine or hydrazine radical or their alkyl derivatives e.g. methyl, ethyl or propyl or their aryl derivatives e.g. phenyl or aralkyl derivatives e.g. benzyl.

The method of the preparation of the derivatives according to the invention consists in treating the desalanyltetaine derivatives of the formula 1, where $R^1$ and $R^2$ have the above mentioned significance and Z is an oxygen atom with hydroxylamine or hydrazine or with their alkyl derivatives e.g. methyl, ethyl or propyl, or their aryl derivatives e.g. phenyl or aralkyl e.g. benzyl. A modification of the method consists in treating the desalanyltetaine of the formula 1, where $R^2$ and Z have the above mentioned significance respectively, and $R^1$ is a hydroxyl group with the chloroethers, preferable with methyl chloroether.

Another modification consists in treating the desalanyltetaine of the formula 1 where $R^1$ and Z have the above mentioned significance respectively, and $R^2$ is a hydrogen atom with carboxylic acids derivatives, capable of acylation of the amine group in the desalanyltetaine derivatives.

Desalanyltetaine / DAT / is a mixture of two isomeric substances, called desalanyltetaine A and B, obtainable from tetaine which itself is a mixture of two isomeric compounds. Both constituents of the mixture have the same functional groups and also posses a similar chemical activity. The semi-synthetic derivatives can be obtained in the same manner as well from the A and B constituents as from their mixture.

The advantage of the derivatives according to the invention consists in their increased stability and apart of this chemical modifications of the desalanyltetaine molecule do not cause the vanishing of the antibiotic activity.

The desalenyltetaine derivatives according to the invention and the process for their preparation are illustrated below.

EXAMPLE I 62 mg / 0.75 milimole / of O-methylhydroxylamine hydrochloride is dissolved in 10 ml of ethyl alcohol and neutralized with potassium bicarbonate until the carbon dioxide formation is finished. The alcoholic solution of O-methyl-hydroxylamine is filtered off from the salt and then is added to the aqueous solution containing 135 mg of tetaine in 20 ml of water. The reaction mixture is left at room temperature for 8 hours. After this time the solvents are evaporated off under reduced pressure the residue is dissolved in methyl alcohol and precipitated by means of thyl ether. The precipitate is centrifugated, washed with ethyl ether and dried under reduced pressure. 115 mg of tetaine O-methyloxime is obtained.

EXAMPLE II

To 10 mg of desalanyltetaine dissolved in 3 ml of water a solution of 8 mg of phenylhydrazine in 5 ml of ethyl alcohol is added. The reaction mixture is kept for 24 hours at room temperature. Thereupon the solvents are evaporated off under reduced pressure and the raw product is purified as in Example I. 11 mg of desalanyltetaine phenylhydrazone is obtained.

EXAMPLE III

To 50 mg of tetaine A dissolved in 10 ml of water 0.013 ml of 80% hydrazne hydrate is added and left for 24 hours at room temperature. The raw tetaine A hydrazone after being separated from the solvents under reduced pressure, is purified as in Example I. Yield 38 mg.

EXAMPLE IV

To the solution of 50 mg of desalanyltetaine in 5 ml of dimethyl formamide 20 mg of methyl-chloromethyl-ether is added at 0° C and left at room temperature for 24 hours maintaining by means of stepwise addition of N-methylmorpholine the pH value in the range of 8–8.5. Thereupon the dimethyl formamide is evaporated under reduced pressure, the residue is in ethyl alcohol dissolved, filtered off and again evaporated. The raw desalanyltetaine methoxymethyl ester is purified by means of ion-exchange chromatography. Yield 45 mg.

EXAMPLE V

To 10 mg of desalanyltetaine A dissolved in 1,5 ml of Michaelis' buffer of pH 8,2 7,5 mg of pivalyl acid chloromethyl ester is added at 0° C and left at room temperature for 24 hours. Thereupon according to the procedure described in Example IV 12 mg of desalanyltetaine a trimethylacetylmethyl ester is obtained.

EXAMPLE VI 13.5 mg of tetaine A is in 2 ml of water dissolved, cooled to 0° C 3 mg of α, α'-dichloro-dimethyl ether in 2 ml of dimethyl formamide added. The reaction and the separation of the resulting tetaine A α,α'-dihydroxydimethyletheric ester is performed according to the procedure described in Example IV. Yield 11 mg.

EXAMPLE VII

To 10 mg of desalanyltetaine B pivalyloxymethyl ester obtained analogically as in Example IV, dissolved in 4 ml of acetone 2.5 mg of O-methylhydroxylamine in 4 ml of ethyl alcohol is added and left at room temperature for 24 hours. After evaporation of the solvents under reduced pressure the raw desalanyltetaine B O-methyloxime pivalyloxymethyl ester is purified on a chromatography column filled with silica-gel, using the ethyl acetatemethanol-water 5:1:1 system as eluent. Yield 5 mg.

EXAMPLE VIII

To 10 mg of tetaine B methoxymethyl ester obtained analogically as in Example IV dissolved in 4 ml of acetone, 2 mg of O-methylhydroxylamine in 4 ml of ethyl alcohol is added. The reaction mixture is left at room temperature for 24 hours and thereupon the tetaine B O-methyloxime methoxymethyl ester is isolated according to the procedure given in Example VII. Yield 6 mg.

EXAMPLE IX 15 mg of tetaine A O-methyloxime is in 1 ml of dimethyl formamide dissolved and at 0° C 4 mg of methyl-chloromethyl ether is added. After 24 hours of reaction at room temperature the solvent is evaporated off under reduced pressure and the resulting raw tetaine A O-methyloxime methoxymethyl ester is purified analogically as in Example VII.

EXAMPLE X 11.4 mg of desalanyltetaine O-methyloxime is dissolved in 1 ml of dimethyl formamide at 0° C and 3 mg of α,α'-dichlorodimethyl ether is added. After 24 hours of reaction at room temperature the solvent is evaporated off under reduced pressure and the resulting raw desalanyltetaine O-methyloxime dihydroxydimethyletheric diester is purified in a manner similar to that described in Example VII. Yield 8 mg.

EXAMPLE XI 11.4 mg of desalanyltetaine B O-methyloxime prepared analogically as in Example I is dissolved in 1 ml of dimethyl formamide at 0° C and while stirring vigorously 5.75 mg D-alanine N-carboxyanhydride is added. The pH value is maintained at 8.5–9 by means of stepwise addition of N-methylmorpholine. After 3 hours the solvent is evaporated under reduced pressure, the residue is dissolved in methyl alcohol and precipitated with ethyl ether. The resulting D-alanyl-desalanyltetaine B O-methyloxime is centrifugated off and washed with ethyl ether. Yield 10 mg.

EXAMPLE XII 11 mg of desalanyltetaine B α,α'-dihydroxydimethyletheric diester is dissolved in 1 ml of dimethyl formamide and while stirring vigorously 10.3 mg of D-α-amino-α-phenylacetic acid chloride hydrochloride and 0.007 ml of triethylamine are added. After 1 hour the solvent is evaporated off under reduced pressure and the raw D-α-amino-α-phenylacetyldesalanyltetaine B α,α'-dihydroxydimethyletheric diester is purified according to the procedure described in Exampe IV. Yield 12 mg.

EXAMPLE XIII 10 mg of desalanyltetane is in 0.5 ml of water dissolved while stirring vigorously at 4° C 9.5 mg of L-phenylalanine-N-carboxyanhydride dissolved in 0.5 ml of tetrahydrofuran is added. After 10 hours the solvent is evaporated off under reduced pressure. L-phenylalanyl-desalanyltetaine is the main product obtained.

EXAMPLE XIV

To 34.2 mg of tetaine acethoxymethyl ester obtained in a manner similar to that described in Example IV dissolved in 3 ml of methanol, 10 mg of acetic anhydride and 10.1 mg of triethylamine are added at 0° C. After 1 hour the solvent is evaporated off and the new acetyltetaine acetoxymethyl ester is purified by means of column chromatography on silica-gel using benzene:ethyl acetate 4:1 system. Yield 31 mg.

EXAMPLE XV 15.2 mg of phenoxyacetic acid is in 2 ml of ethyl acetate dissolved, cooled to −10° C. Thereupon 10.1 mg of N-methylmorpholine and 13.6 mg of isobutyl chloroformate are added. After 10 minutes at the same temperature 37.1 mg of tetaine oxime acetoxymethyl ester in 2 ml of dimethyl formamide is added and the reaction is continued for 1 hour at −20° C and for another 1 hour at room temperature. Thereupon the solvents are evaporated off under reduced pressure and the resulting raw phenoxyacetyltetaine oxime acetoxymethyl ester is purified by means of column chromatography on silica-gel using benzene:ethyl acetate 4:1 system. Yield 35 mg.

Similar methods were used for the preparation of further desalanyltetaine derivatives which are listed below.

| N° | Desalanyltetaine derivative | Preparation method |
|----|----------------------------|--------------------|
| 1. | desalanyltetaine O-methyloxime | I |
| 2. | tetaine O-ethyloxime | I |
| 3. | tetaine O-propyloxime | I |
| 4. | tetaine O-benzyloxime | I |
| 5. | desalanyltetaine oxime | I |
| 6. | desalanyltetaine hydrazone | I |
| 7. | tetaine methoxymethyl ester | IV |
| 8. | tetaine ethoxymethyl ester | IV |
| 9. | tetaine isopropyloxymethyl ester | IV |
| 10. | tetaine benzyloxymethyl ester | IV |
| 11. | tetaine cyclohexyloxymethyl ester | IV |
| 12. | tetaine α-acetoxyethyl ester | IV |
| 13. | tetaine α-pivalyloxyethyl ester | IV |
| 14. | tetaine α-pivalyloxy-α-phenylmethyl ester | IV |
| 15. | tetaine α-pivalyloxy-β-phenylethyl ester | IV |
| 16. | tetaine O-methyloxime acetoxymethyl ester | IX |
| 17. | tetaine O-methyloxime pivalyloxymethyl ester | IX |
| 18. | tetaine O-methyloxime cyclohexyloxymethyl ester | IX |
| 19. | phenylacetyltetaine pivalyloxymethyl ester | XV |
| 20. | furylacetyltetaine pivalyloxymethyl ester | XV |
| 21. | thienylacetyltetaine pivalyloxymethyl ester | XV |
| 22. | L-phenylalanyl-desalanyltetaine pivalyloxymethyl ester | XI |

| N° | Desalanyltetaine derivative | Preparation method |
|---|---|---|
| 23. | L-phenylalanyltetaine pivalyloxymethyl ester | XI |
| 24. | phenoxyacetyldesalanyltetaine acetoxymethyl ester | XV |
| 25. | L-phenylalanyltetaine O-methyloxime | I |

All the obtained substances were tested using thin-layer chromatography and biochromatography methods. Their identity was confirmed by mass spectra using the field desorption technique.

What we claim is:

1. Compounds of the formula

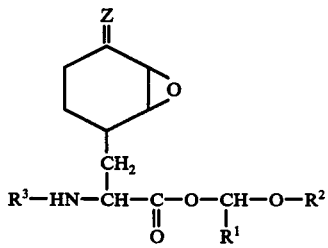

wherein $R^1$ is hydrogen, $R^2$ is selected from the group consisting of alkyl of form 1 to 6 carbon atoms, acyl of from 1 to 6 carbon atoms and benzyl, $R^3$ is selected from the group consisting of hydrogen, α-aminoacyl, acetylaminoacyl, phenoxyacetylaminoacyl, acetyl and substituted acetyl, and Z is oxygen.

* * * * *